United States Patent
Meadows et al.

(10) Patent No.: US 6,381,496 B1
(45) Date of Patent: Apr. 30, 2002

(54) PARAMETER CONTEXT SWITCHING FOR AN IMPLANTED DEVICE

(75) Inventors: Paul M. Meadows, La Crescenta; Carla M. Mann, Los Angeles, both of CA (US)

(73) Assignee: Advanced Bionics Corporation, Sylmar, CA (US)

(*) Notice: Subject to any disclaimer, the term of this patent is extended or adjusted under 35 U.S.C. 154(b) by 0 days.

(21) Appl. No.: 09/668,925

(22) Filed: Sep. 25, 2000

Related U.S. Application Data

(60) Provisional application No. 60/156,979, filed on Oct. 1, 1999.

(51) Int. Cl.[7] .................................................. A61N 1/08
(52) U.S. Cl. ........................................................... 607/59
(58) Field of Search ............................... 607/59, 60, 30

(56) References Cited

U.S. PATENT DOCUMENTS

| | | | |
|---|---|---|---|
| 3,646,940 A | 3/1972 | Timm et al. ................. | 128/421 |
| 3,724,467 A | 4/1973 | Avery et al. ................. | 128/418 |
| 3,822,708 A | 7/1974 | Zilber ......................... | 128/419 |
| 4,338,945 A | 7/1982 | Kosugi et al. .............. | 128/421 |
| 4,379,462 A | 4/1983 | Borkan et al. .............. | 128/786 |
| 4,735,204 A | 4/1988 | Sussman et al. ........... | 128/419 |
| 5,121,754 A | 6/1992 | Mullett ........................ | 128/786 |
| 5,417,719 A | 5/1995 | Hull et al. ................... | 607/46 |
| 5,433,736 A | 7/1995 | Nilsson ....................... | 607/59 |
| 5,501,703 A | 3/1996 | Holsheimer et al. ........ | 407/46 |
| 5,626,629 A | 5/1997 | Faltys et al. ................ | 607/57 |
| 5,713,937 A * | 2/1998 | Nappholz et al. | |
| 5,973,968 A | 10/1999 | Shu et al. ................... | 365/195 |
| 6,052,624 A | 4/2000 | Mann .......................... | 607/46 |
| 6,120,467 A | 9/2000 | Schallhorn .................. | 600/595 |
| 6,249,703 B1 * | 6/2001 | Stanton et al. | |

* cited by examiner

*Primary Examiner*—Scott M. Getzow
(74) *Attorney, Agent, or Firm*—Bryant R. Cold

(57) ABSTRACT

An implant device provides context switching, meaning the ability to change one set of operational parameters for another. The implant device is controlled by a set of operational parameters. The patient may swap the current set of operational parameters with another set of operational parameters. Further, the implant device may include a time-of-day clock, and/or a sensor, and is configured to automatically change its operational parameters from one set of operational parameters to another at certain times of the day, week, or month, or upon the occurrence of certain prescribed events. In one embodiment, the patient may define selected operational parameters within a new set of operational parameters for use with the implant device, providing such patient-defined parameters remain within set limits. The ability to change the current operational parameter set (OPS) is achieved, in a first embodiment, by including memory circuitry within the implant device wherein a plurality of OPS's are stored. Upon receipt of an appropriate command, manually provided by the patient user through a hand-help programmer, or automatically generated by time-of-day or sensor circuits within the implant device, the current OPS is exchanged by another OPS. In a second embodiment, a plurality of OPS's are externally stored, e.g., in a hand-held programming device, and only the currently-used OPS is stored in the implant device. Changes to the OPS are made by transmitting the replacement OPS to the implant device through a telemetry link established with the implant device from the hand-held programming device. When the patient wishes to change the OPS, he manually activates the appropriate controls on the hand-held programming device, and such activation causes the new OPS to be telemetered to the implant device, where it replaces the current OPS.

18 Claims, 8 Drawing Sheets

PARAMETER CONTEXT SWITCHING FOR AN IMPLANTED DEVICE

The present application claims the benefit of U.S. Provisional Patent Application Ser. No. 60/156,979, filed Oct. 1, 1999, which application is incorporated herein by reference.

BACKGROUND OF THE INVENTION

The present invention relates to an implant device, e.g., a spinal cord stimulation (SCS) system or other programmable implant device. A spinal cord stimulation system treats chronic pain by providing electrical stimulation pulses from an electrode array placed epidurally near a patient's spinal cord. Such a spinal cord system includes several components, ranging from implantable and external components, surgical tools, and software. The present invention emphasizes the manner in which such SCS system, or any other programmable implant system, manages and changes its operational parameters.

The operation of an implanted device depends upon the storage and use of certain operational parameters. For a pulse generator system, e.g., an SCS system, these parameters might include: stimulation pulse amplitudes, pulse durations, channel frequencies, electrode configurations, ramp rates and treatment times, and the like. For a drug delivery system, such operational parameters might further include additional parameters related to the type of drug delivery, the drug medication rate of delivery, all of which may vary over the course of a day. When it is necessary to change the operation of such an implanted device, it is necessary to modify the parameters used by the device as it carries out its intended function, e.g., delivering stimulation pulses, delivering drug medication, sensing physiological activity, or the like. The present invention relates to the manner in which these operational parameters, used by the implant system as it carries out its intended function, are changed and managed. While the invention will be described in the context and background of a spinal cord stimulation system, it is to be understood that the invention has applicability, and can be used with, numerous different types of implant devices and systems, including all types of neural stimulators and sensors, deep brain stimulators, cochlear stimulators, drug delivery systems, muscle tissue stimulators, and the like.

Spinal cord stimulation (SCS) is a well accepted clinical method for reducing pain in certain populations of patients. SCS systems typically include an implanted pulse generator, lead wires, and electrodes connected to the lead wires. The pulse generator generates electrical pulses that are delivered to the dorsal column fibers within the spinal cord through the electrodes which are implanted along the dura of the spinal cord. The attached lead wires exit the spinal cord and are tunneled around the torso of the patient to a sub-cutaneous pocket where the pulse generator is implanted.

Spinal cord and other stimulation systems are known in the art. For example, in U.S. Pat. No. 3,646,940, there is disclosed an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

In U.S. Pat. No. 3,724,467, an electrode implant is disclosed for the neuro-stimulation of the spinal cord. A relatively thin and flexible strip of physiologically inert plastic is provided with a plurality of electrodes formed thereon. The electrodes are connected by leads to an RF receiver, which is also implanted, and which is controlled by an external controller. The implanted RF receiver has no power storage means, and must be coupled to the external controller in order for neuro-stimulation to occur.

In U.S. Pat. No. 3,822,708, another type of electrical spinal cord stimulating device is shown. The device has five aligned electrodes which are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds ($\mu$s) in width with a repetition rate of from 5 to 200 pulses per second (pps). A patient-operable switch allows the patient to change which electrodes are activated, i.e., which electrodes receive the current stimulus, so that the area between the activated electrodes on the spinal cord can be adjusted, as required, to better block the pain.

Other representative patents that show spinal cord stimulation systems or electrodes include U.S. Pat. Nos. 4,338,945; 4,379,462; 5,121,754; 5,417,719 and 5,501,703.

The dominant SCS products that are presently commercially available attempt to respond to three basic requirements for such systems: (1) providing multiple stimulation channels to address variable stimulation parameter requirements and multiple sites of electrical stimulation signal delivery; (2) allowing modest to high stimulation currents for those patients who need it; and (3) incorporating an internal power source with sufficient energy storage capacity to provide years of reliable service to the patient. Unfortunately, not all of these features are available in any one device. For example, one well-known device has a limited battery life at only modest current outputs, and has only a single voltage source, and hence only a single stimulation channel, which must be multiplexed in a fixed pattern to up to four electrode contacts. Another well-known device offers higher currents that can be delivered to the patient, but does not have a battery, and thus requires the patient to wear an external power source and controller. Even then, such device still has only one voltage source, and hence only a single stimulation channel, for delivery of the current stimulus to multiple electrodes through a multiplexer. Yet a third known device provides multiple channels of modest current capability, but does not have an internal power source, and thus also forces the patient to wear an external power source and controller.

All such known devices further use different approaches for modifying or changing the operational parameters that control operation of the device. Some allow only the physician or surgeon or other medical professional to make any changes in the operating parameters, thereby making it necessary for the user (the "patient" who receives the benefit from the implant device) to schedule an appointment with such professional if any changes are needed. Often, the changes needed by the patient are relatively benign (insofar as the safety of the altered treatment is concerned), and could easily be made by the patient himself or herself if only the implant device provided such capability. On the other hand, the patient must not be given carte blanche to make wide spread changes in the operating parameters, else he or she could inadvertently set up a treatment regimen delivered by the implant device that could be injurious to the patient's health or damaging to the device. Thus, what is needed is a way for the patient to readily make appropriate changes to the operating parameters of an implant device so long as such operating parameter changes maintain the device operation within safe operating limits. The operating limits should only be changeable by the physician or other medical-professional clinician.

SUMMARY OF THE INVENTION

The present invention addresses the above and other needs by providing an implant device having the ability to perform context switching. As used herein, "context switching" means changing one set of operational parameters to another.

In accordance with one aspect of the invention, an implant device is controlled by a set of operational parameters, and the patient may advantageously swap the current set of operational parameters with another set of operational parameters.

In accordance with another aspect of the invention, the implant device further includes a time-of-day clock, and/or sensor, and automatically changes its operational parameters from one set to another set at certain times of the day, week, or month, or upon the occurrence of certain prescribed events. For example, a nighttime operational parameter set that provides a slower stimulation rate or stimulation frequency might be automatically invoked to replace a daytime operational parameter set that defines a faster stimulation rate or stimulation frequency at a prescribed hour of the day, e.g., 10:00 PM. Similarly, the daytime operational parameter set would replace the nighttime operational parameter set at another prescribed hour of the day, e.g., 6:00 AM. Alternatively, or conjunctively, if certain threshold limits are sensed by a physiological or other sensor that is included within or coupled to the implant device, then such sensing event may automatically trigger a new set of operational parameters for the implant device aimed at treating the condition sensed (the "event"), by the sensor.

In accordance with yet another aspect of the invention, each set of operational parameters that may be selected by the patient, or that is automatically invoked by the device at certain times of the day or upon the occurrence of certain events, does not exceed safe operating limits of the device as prescribed by the manufacturer of the device and/or the attending physician or other competent medical personnel. (In this context, "safe operating limits" refers both to safe treatment protocols for the particular patient, as well as safe operating conditions for the design of the particular implant device.)

In accordance with still an additional aspect of the invention, the patient may define a new set of operational parameters for use with the implant device so long as all parameters included within the newly defined set of operational parameters remain within prescribed limits as set by the manufacturer of the device and/or as programmed by the attending physician or other competent medical personnel.

In one embodiment of the invention, the ability to change the current operational parameter set (OPS) of the implant device is provided by including memory circuitry within the implant device wherein a plurality of OPS's are programmably stored. Upon receipt of an appropriate command, which may be manually provided by the patient through, e.g., a hand-help programmer, or automatically generated by time-of-day or sensor circuits within (or coupled to) the implant device, the current OPS is exchanged by another OPS. Each OPS stored in the implant device is limited by an external programming unit to be within safe operating limits.

In another embodiment of the invention, a plurality of OPS's are externally stored, e.g., in a hand-held programming device, and only the currently-used OPS is stored in the implant device. Changes to the OPS are made by transmitting the replacement OPS to the implant device through a telemetry link established with the implant device from the hand-held programming device. Thus, when the patient wishes to make a change in the OPS, he or she manually activates the appropriate controls on the hand-held programmer (HHP), and such activation causes the new OPS to be telemetered to the implant device, where it replaces the current OPS. For this embodiment, when an "automatic" change to the OPS is called for, e.g., when a sensor detects the occurrence of a prescribed event that signals the need to change the OPS, such change may occur at the next available time a telemetry link is established between the HHP and implant device.

It is a feature of the present invention that the implant system also allow the user, or patient, to define a new operational parameter set (OPS) which, once defined, may be selected to replace the current operational parameter set. In accordance with such feature, the patient may only be allowed to change certain ones of the individual parameters included within the OPS, and changes to those parameters are automatically limited to fall within pre-defined safe operating limits. Therefore, should the patient attempt to set an individual parameter outside of the pre-defined safe operating limits, then the parameter value is set to its limit value closest to the out-of-limit value attempted by the patient. For example, if the safe operating range for the pulse width of a stimulating pulse is between 10 $\mu$s and 1 millisecond (ms), and should the patient attempt to set the pulse width to 10 ms, then the pulse width parameter in the newly defined OPS would be set to 1 ms, the maximum limit. Similarly, should the patient attempt to set the pulse width to 5 $\mu$s, then the pulse width parameter in the OPS would be set to 10 $\mu$s, the minimum limit. In this manner, the patient is allowed to define a new OPS for use within the implant device, but the individual parameters within such newly-defined OPS are limited to pre-defined safe values.

An advantage of the invention is that enhanced utility is provided in an implant device. More particularly, changes to the operating parameter set of the implant device may be easily made and accommodated and executed and require little, if any, intervention by the patient.

An additional advantage of the invention, in accordance with one embodiment thereof, is that the implant device allows a patient to define a new operating parameter set for use by the implant device. Advantageously, the newly-defined parameters included within the new operating parameter set are automatically restricted or limited so as to all fall within safe operating limits. In this manner, it thus becomes impossible for the patient to inadvertently, ignorantly, or mistakenly define a new operating parameter set for the implant device that might prove to be detrimental or harmful to the patient or to the device.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, and as previously indicated, it is emphasized that the present invention relates to parameter context switching, i.e., defining and/or selecting different operational parameter sets for use by an implant device. The invention will be described with reference to the implanted pulse generator (IPG) and hand-held programmer (HHP) of a spinal cord stimulation (SCS) system. An exemplary SCS system is described more fully in U.S. patent application Ser. No. 09/626,010, filed Jul. 26, 2000, incorporated herein by reference. It is to be understood, however, that the present invention is not limited for use just within an SCS system of the type described in the referenced patent application. Rather, the invention has broad applicability, and may be used with numerous different types of implant devices and/or systems, including all types of neural stimulators and sensors, deep brain stimulators, cochlear stimulators, drug delivery systems, muscle tissue stimulators, and the like, regardless of whether such systems incorporate implantable or external components. That is, the invention may be used with implantable systems, non-implantable systems, or systems made up of a combination of implantable and external components.

Figure 1:
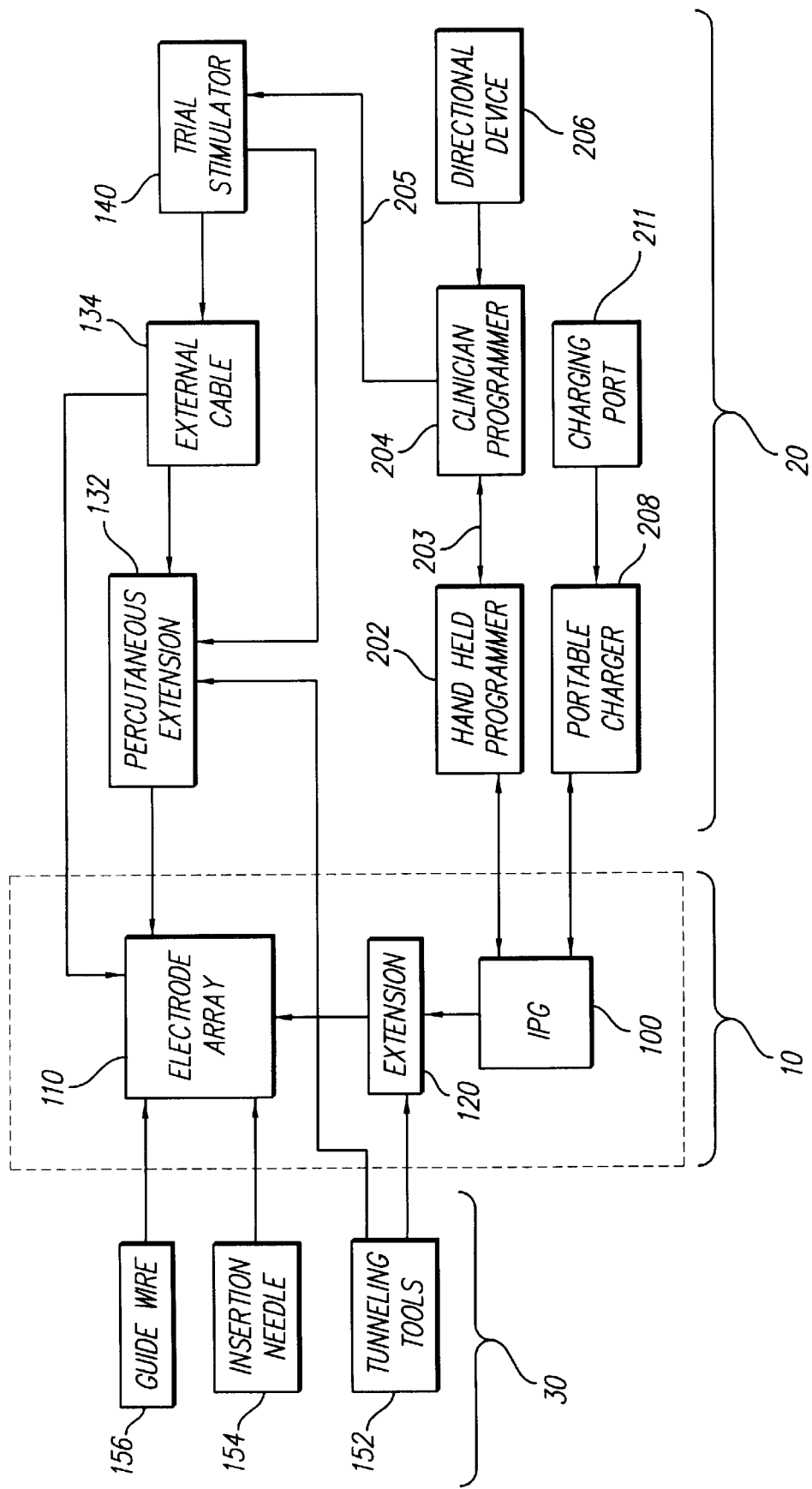
FIG. 1 is a block diagram that illustrates the various implantable, external, and surgical components of a representative spinal cord stimulating (SCS) system, including an implantable pulse generator (IPG), which IPG is exemplary of one type of implant device with which the present invention may be used.

Turning first to FIG. 1, there is shown a block diagram that illustrates the various components of an exemplary SCS system, including the IPG and HHP used with such system. These components may be subdivided into three broad categories: (1) implantable components 10, (2) external components 20, and (3) surgical components 30. As seen in FIG. 1, the implantable components 10 include an implantable pulse generator (IPG) 100, an electrode array 110, and (as needed) an extension 120. The extension 120 is used to electrically connect the electrode array 110 to the IPG 100. The IPG 100, described more fully below in connection with FIG. 4, comprises a rechargeable, multichannel, 16 contact, telemetry-controlled, pulse generator housed in a rounded titanium case. A novel tool-less connector that forms an integral part of the IPG 100 allows the electrode array 110 or extension 120 to be detachably secured, i.e., electrically connected, to the IPG 100. This connector may be of the type described in U.S. patent application Ser. No. 09/239,926, filed Jan. 28, 1999, incorporated herein by reference.

The IPG 100 contains stimulating electrical circuitry ("stimulating electronics"), a power source, e.g., a rechargeable battery, and a telemetry system. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted, the lead system 110 and lead extension 120 are intended to be permanent. In contrast, the IPG 100 may be replaced when its power source fails or is no longer rechargeable.

Figure 2:
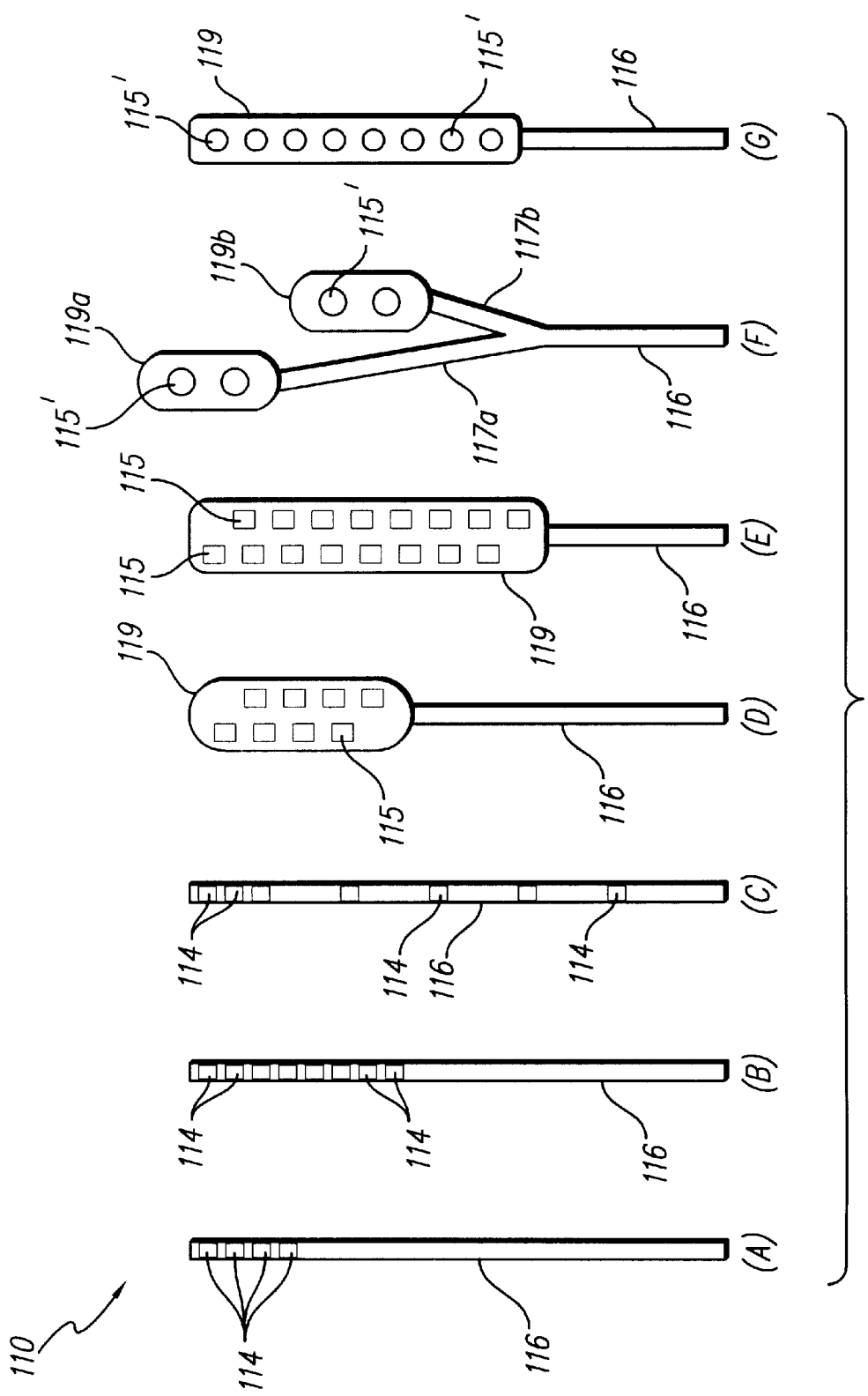
FIG. 2 illustrates examples of various types of electrode arrays that may be used with the SCS system of FIG. 1.

Advantageously, the IPG 100 can provide electrical stimulation through a multiplicity of electrodes, e.g., sixteen electrodes, included within the electrode array 110. Different types of electrode arrays 110 that may be used with the invention are depicted in FIG. 2. A common type of electrode array 110, for example, is the "in-line" lead, as shown at (A), (B), and (C) in FIG. 2. An in-line lead includes individual electrode contacts 114 spread longitudinally along a small diameter flexible cable or carrier 116. The flexible cable or carrier 116 has respective small wires embedded (or otherwise carried therein) for electrically contacting each of the individual electrode contacts. The advantage of an in-line lead relates to its ease of implantation, i.e., it can be inserted into the spinal canal through a small locally-anesthetized incision while the patient is kept awake. When the patient is awake, he or she can provide valuable feedback as to the effectiveness of stimulation applied to a given electrode contact or contacts 114 for a given positioning of the array 110. One of the disadvantages of the in-line lead is that it is prone to migrating in the epidural space, either over time or as a result of a sudden flexion movement. Such migration can disadvantageously change the location and nature of the paresthesia and the required stimulation level. Either or both of the these conditions may require reprogramming of the IPG 100 and/or surgical correction (repositioning) of the electrode array 110. Note, as used herein, the term "paresthesia" refers to that area or volume of the patient's tissue that is affected by the electrical stimuli applied through the electrode array. The patient may typically describe or characterize the paresthesia as an area where a tingling sensation is felt.

To overcome the migration problems associated with an in-line electrode, a different type of electrode array 110 may be used, known as a paddle lead. Various types of paddle leads are illustrated at (D), (E), (F) and (G) of FIG. 2. In general, each type of paddle lead is shaped with a wide platform 119 on which a variety of electrode contact configurations or arrays are situated. For example, the paddle lead shown at (D) in FIG. 2 has two columns of four rectangular-shaped electrode contacts 115 carried on a wide platform 119, with the electrode contacts in one column being offset from the electrode contacts in the other column. (Here, the term "offset" refers to the vertical position of the electrode contacts, as the leads are oriented in FIG. 2.) The flexible cable or carrier 116 carries wires from each electrode contact to a proximal end of the paddle lead (not shown), where such wires may be connected to the IPG 100 (or to a lead extension 120, which in turn connects to the IPG 100). The paddle lead shown at (E) in FIG. 2 similarly has two columns of eight electrode contacts 115 in each row, with the electrode contacts in one column being offset from the electrode contacts in the other column, and with each electrode contact being connected to one or more wires carried in the flexible cable or carrier 116.

Still referring to FIG. 2, other types of paddle leads are illustrated. As seen at (F) in FIG. 2, one type of paddle lead has its carrier or cable 116 branch into two separate branches 117a and 117b, with a wide platform 119a and 119b being located at a distal end of each branch. Within each wide platform 119a and 119b an array of at least two circular-shaped electrode contacts 115' is situated. As seen in (G) in FIG. 2, another type of paddle lead has a wide platform 119 at its distal end on which a single column of circular-shaped electrode contacts 115' is situated.

A preferred type of SCS system, such as the one shown in FIG. 1, preferably has the ability to support more than one lead with two or more channels. Here, a "channel" is defined as a specified electrode, or group of electrodes, that receive a specified pattern or sequence of stimulus pulses. Thus, where more than one "channel" is available, each channel may be programmed to provide its own specified pattern or sequence of stimulus pulses to its defined electrode or group of electrodes. In operation, all of the stimulus patterns applied through all of the channels of such multi-channel system thus combine to provide an overall stimulation pattern that is applied to the tissue exposed to the individual electrodes of the electrode array(s).

There are many instances when it is advantageous to have multiple channels. For example, left and right sides, or upper and lower extremities, may require different stimulus parameter settings. Low back pain typically requires a different stimulation site and stimulation parameters than any of the extremities. Moreover, many patients exhibit conditions better suited to horizontal stimulation paths, while other patients may have conditions better suited to vertical stimulation paths. Therefore, having multiple channels that may be connected to multiple electrodes, positioned within one or more electrode arrays, so as to cover more tissue/nerve area, greatly facilitates providing the type of stimulation pattern and stimulation parameters needed to treat a particular patient. However, it should be noted, that the present invention may also be used in single-channel systems, even though the preferred system employs multiple channels.

The electrode array 110 and its associated lead system typically interface with the implantable pulse generator (IPG) 100 via a lead extension system 120. As needed, e.g., for testing and/or fitting purposes, the electrode array 110 may also interface with an external trial stimulator 140 through one or more percutaneous lead extensions 132, connected to the trial stimulator 140 through an external cable 134. In this manner, the individual electrodes included within the electrode array 110 may receive an electrical stimulus from either the trial stimulator 140 or the IPG 100.

As suggested in the block diagram of FIG. 1, the lead extension(s) 120, as well as the percutaneous extension(s) 132 are inserted through the patient's tissue through the use of appropriate surgical components 30, and in particular through the use of tunneling tools 152, as are known in the art, or as are especially developed for purposes of spinal cord stimulation systems (such as is disclosed in U.S. patent application Ser. No. 60/166,560, filed Nov. 19, 1999). In a similar manner, the electrode array 110 is implanted in its desired position, e.g., adjacent the spinal column of the patient, through the use of an insertion needle 154 and a guide wire 156.

Figure 3:
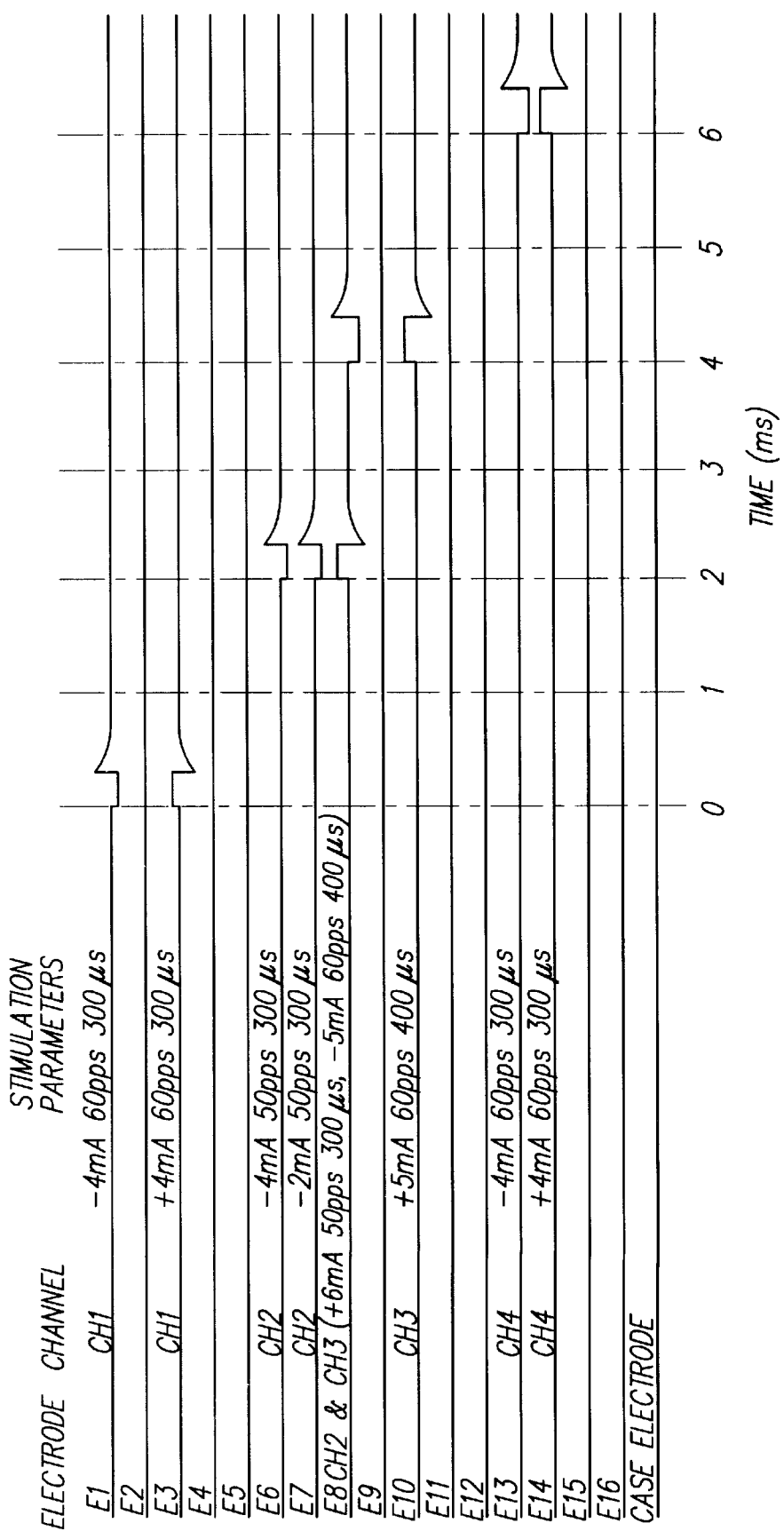
FIG. 3 is a timing waveform diagram that depicts representative current waveforms that may be applied to various ones of the electrode contacts of the electrode arrays through one or more stimulous channels.

One possible depiction of the operation of multiple channels used to provide a stimulus pattern through multiple electrodes is illustrated in FIG. 3. FIG. 3 assumes the use of an electrode array 110 having sixteen electrodes connected to the implantable pulse generator (IPG) 100. In addition to these sixteen electrodes, which are numbered E1 through E16, a case electrode (or return electrode) is also available. In FIG. 3, the horizontal axis is time, divided into increments of 1 ms, while the vertical axis represents the amplitude of a current pulse, if any, applied to one of the sixteen electrodes. Thus, for example, at time t=0 ms, FIG. 3 illustrates that a current pulse of 4 milliamps (mA) appears on channel 1 at electrode E1 and E3. FIG. 3 further shows that this current pulse is negative (−4 mA) on electrode E1 and positive (+4 mA) on electrode E3. Additionally, FIG. 3 shows that the stimulation parameters associated with this current pulse are set at a rate of 60 pps, and that the width of the pulse is about 300 µs.

Still with reference to FIG. 3, it is seen that at time t=2 ms, channel 2 of the IPG 100 is set to generate and apply a 6 mA pulse, having a repetition rate of 50 pps and a width of 300 µs, between electrode E8 (+6 mA) and electrodes E6 and E7 (−4 mA and −2 mA, respectively). That is, channel 2 of the IPG supplies a current pulse through electrode E8 (+6 mA) that is shared on its return path through electrode E6 (−4 mA) and electrode E7 (−2 mA).

As further seen in FIG. 3, at time t=4 ms, channel 3 of the IPG 100 is set to generate and supply a 5 mA pulse to electrode E10 (+5 mA) which is returned through electrode E8 (−5 mA). This pulse has a rate of 60 pps, and a width of 400 µs. Similarly, it is seen that at time t=6 ms, channel 4 of the IPG is set to generate and supply a 4 mA pulse to electrode E14 (+4 mA) which is returned through electrode E13 (−4 mA). This channel 4 pulse has a rate of 60 pps and a width of 300 µs.

The particular electrodes used with each of the four channels of the IPG 100 illustrated in FIG. 3 are only exemplary of many different combinations of electrode pairing and electrode sharing that could be used. That is, any channel of the IPG may be programmably connected to any grouping of the electrodes, including the reference (or case) electrode. While it is common that only two electrodes be paired together for use by a given channel of the IPG, as is the case with channels 1, 3 and 4 in the example of FIG. 3, it is to be noted that any number of electrodes may be grouped and used by a given channel. When more than two electrodes are used with a given channel, the sum of the current sourced from the positive electrodes should be equal to the sum of the current sunk (returned) through the negative electrodes, as is the case with channel 2 in the example of FIG. 3 (+6 mA sourced from electrode E8, and a total of −6 mA sunk to electrodes E6 [−4 mA] and E7 [−2 mA]).

It is also noted that, in addition to the types of pulses shown in FIG. 3, other types of pulses, and pulse stimulation patterns, may be applied through the electrodes, as needed or desired for a particular application. A representation of exemplary types of pulses, and pulse patterns, that may be applied through an array of implanted electrodes is shown, for example, in U.S. Pat. No. 5,601,617, incorporated herein by reference.

Figure 4:
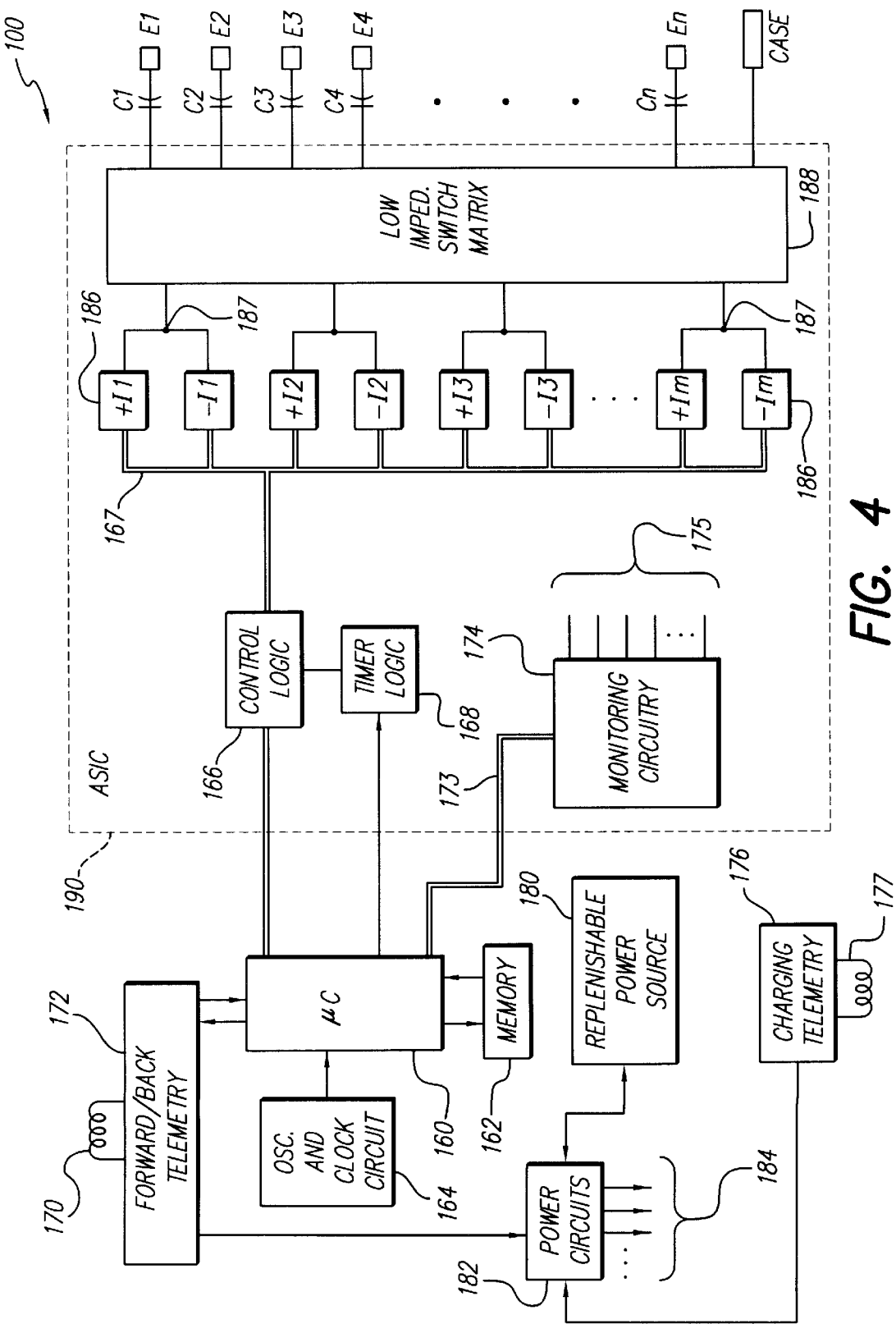
FIG. 4 is a block diagram that functionally illustrates the main components of one embodiment of an implantable pulse generator (IPG) that may be used with an SCS system in accordance with the invention.

Turning next to FIG. 4, a block diagram is shown that illustrates the main components of an implantable pulse generator, or IPG, 100 used with an exemplary SCS system. As seen in FIG. 4, the IPG includes a microcontroller ($\mu$C) 160 connected to memory circuitry 162, The $\mu$C 160 typically comprises a microprocessor and associated logic circuitry, which in combination with control logic circuits 166, timer logic 168, and an oscillator and clock circuit 164, generate the necessary control and status signals which allow the $\mu$C 160 to control the operation of the IPG in accordance with a selected operating program and operational parameter set (OPS). The operational parameter set for an IPG 100 of the type shown in FIG. 4 includes parameter values that define, e.g., pulse amplitude, pulse width (duration), channel frequency, electrode configuration, ramp rate, treatment (stimulation) time, and the like. The operating program and OPS are programably stored within different locations of the memory 162 by transmitting an appropriate modulated carrier signal through a receiving coil 170 and forward/back telemetry circuitry 172 from an external programing unit, e.g., a handheld programmer 202 and/or a clinician programmer 204, assisted as required through the use of a directional device 206 (see FIG. 1). (The handheld programmer is thus considered to be in "telecommunicative" contact with the IPG; and the clinician programmer is likewise considered to be in telecommunicative contact with the handheld programmer, and through the handheld programmer, with the IPG.) The forward/backward telemetry circuitry 172 demodulates the carrier signal it receives through the coil 170 to recover the programming data, e.g., the operating program and/or the OPS, which are then stored within known addresses of the memory 162, or within other memory elements (not shown) distributed throughout the IPG 100.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes E1 . . . En, and the like. Informational data sensed through the monitoring circuit 174 may be sent to a remote location external the IPG (e.g., a non-implanted location) through the microcontroller 160, the forward/back telemetry circuitry 172, and the coil 170.

The operating power for the IPG 100 is derived from a replenishable power source 180, e.g., a rechargeable battery and/or a supercapacitor. Such power source 180 provides an unregulated voltage to power circuits 182. The power circuits 182, in turn, generate the various voltages 184, some of which are regulated and some of which are not, as needed by the various circuits located within the IPG. The power circuits 182 further selectively direct energy contained within a charging signal, received through charging coil 177 and charging telemetry circuit 176, to the replenishable power source 180 during a charging mode of operation. In this way, the power source 180 may be recharged when needed.

In one embodiment, the power source 180 of the IPG 100 comprises a rechargeable battery. Recharging occurs inductively through charging coil 177 from an external charger 208 (FIG. 1) to an implant depth of approximately 2–3 cm. The external charger 208 may be coupled to a charging port 211 (FIG. 1).

The IPG 100 is typically able to monitor and telemeter the status of its replenishable power source 180 (e.g., rechargeable battery) each time a communication link is established with the external patient programmer (hand-held programmer) 202. Such monitoring not only identifies how much charge is left, but also charge capacity. Typically, a telecommunicative link is established, and hence battery monitoring may occur, each time a programming event occurs, e.g., each time the patient or medical personnel enable/disable the IPG 100, or change a stimulus parameter.

The power circuits 182 advantageously include protection circuitry that protects the replenishable power source 180 from overcharging. Also, safeguarding features are incorporated that assure that the power source is always operated in a safe mode upon approaching a charge depletion. Potentially endangering failure modes are avoided and prevented through appropriate logic control that is hard-wired into the device, or otherwise set in the device in such a way that the patient cannot override them.

Still with reference to FIG. 4, it is seen that a plurality m of independent current source pairs, 186+I1, 186–I1, 186+I2, 186–I2, 186+I3, 186–I3, . . . 186+Im, 186–Im are coupled to the control logic 166 via control bus 167. One current source of each pair of current sources functions as a positive (+) current source, while the other current source of each pair functions as a negative (−) current source. The output of the positive current source and the negative current source of each pair of current sources 186 is connected to a common node 187. This common node 187, in turn, is connected through a low impedance switching matrix 188 to any of n electrode nodes E1, E2, E3, . . . En, through respective coupling capacitors C1, C2, C3, . . . Cn. Through appropriate control of the switching matrix 188, any of the m current source nodes 187 may be connected to any of the electrode nodes E1, E2, E3, . . . En. Thus, for example, it is possible to program the current source 186+I1 to produce a pulse of +4 mA (at a specified rate and for a specified duration), and to synchronously program the current source 186–I2 to similarly produce a pulse of −4 mA (at the same rate and pulse width), and then (through the switching matrix 188) connect the 186+I1 node to electrode node E3 and the 186–I2 node to electrode node E1 at relative time t=0 ms (and at a recurring rate thereafter) in order to realize the operation of channel 1 depicted in the timing diagram of FIG. 3. In a similar manner, the operation of channels 2, 3 and 4 shown in FIG. 3 may likewise be realized.

Figure 5:
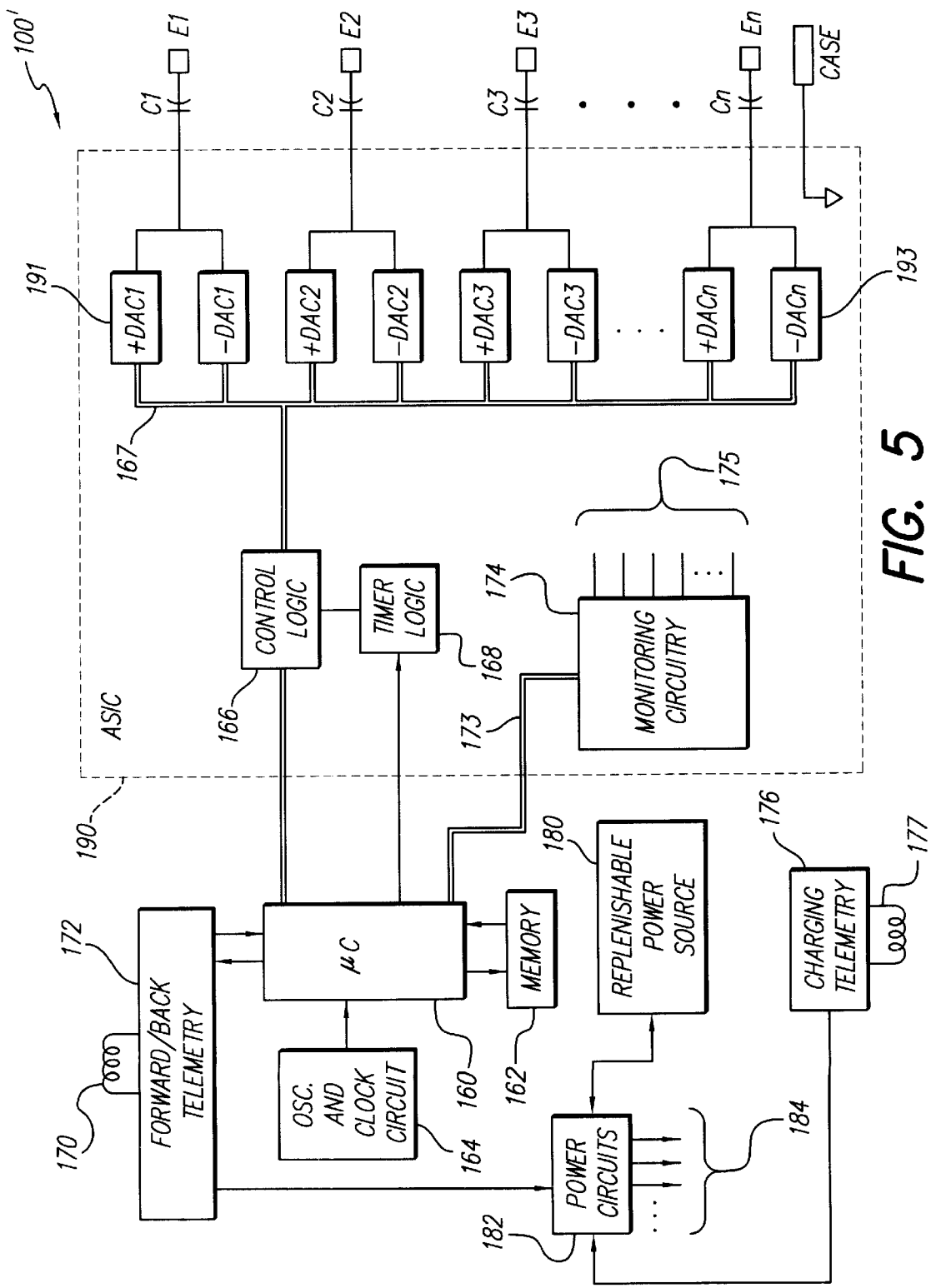
FIG. 5 is a block diagram that functionally illustrates the main components of another embodiment of an implantable pulse generator (IPG) that may be used with an SCS system in accordance with the invention.

An alternate functional block diagram of an IPG 100' is shown in FIG. 5. The front end elements included in FIG. 5, e.g., the coil 170, forward/back telemetry circuit 172, microcontroller 160, memory 162, oscillator and clock circuit 164, monitoring circuitry 174, timer logic 168, control logic 166, charging coil 177, charging telemetry circuit 176, power circuits 182, and power source 180, are the same as previously described in connection with FIG. 4. The IPG 100' shown in FIG. 5 differs from the IPG 100 shown in FIG. 4 in the manner in which an output current having a specified amplitude, pulse width, and timing relationship, is directed to a selected electrode. As seen in FIG. 5, each electrode E1, E2, E3 . . . En, is connected, through a respective coupling capacitor C1, C2, C3 . . . Cn, to a positive current DAC (digital to analog converter) 191 and a negative current DAC 193. That is, electrode E1 is connected through coupling capacitor C1 to positive current +DAC1 and negative current −DAC1. Similarly, electrode E2 is connected through coupling capacitor C2 to positive current +DAC2 and negative current −DAC2; electrode E3 is connected through coupling capacitor C3 to positive current +DAC3 and negative current −DAC3; and so on, with electrode En being connected through coupling capacitor Cn to positive current +DACn and negative current −DACn. The control logic 166 controls each of the positive DACs 191 and negative DACs 193 so that an electrical current having a specified amplitude and polarity is directed to a selected electrode for a specified time period and repetition rate. The circuit configuration of the IPG 100' shown in FIG. 5 thus eliminates the need for the low impedance switching matrix 188, shown in embodiment of the IPG 100 depicted in FIG. 4. The positive and negative current DACs 191 and 193 may be realized using circuitry as described in pending U.S. patent application Ser. No. 09/338,700, filed Jun. 23, 1999, now issued as U.S. Pat. No. 6,181,969.

As described above, whether the IPG configuration of FIG. 4 or FIG. 5 is employed, it is seen that any of the n electrodes may be assigned to up to k possible groups (where k is an integer corresponding to the number of channels, and in a preferred embodiment is equal to 4). Moreover, any of the n electrodes can operate, or be included in, any of the k channels. The channel identifies which electrodes are selected to synchronously source or sink current in order to create an electric field. Amplitudes and polarities of electrodes on a channel may be adjusted, e.g., as controlled by the current operational parameter set (OPS) used by the IPG. The OPS also typically assigns a pulse rate and pulse width for the electrodes of a given channel.

Hence, it is seen that each of the n programmable electrode contacts can be programmed, through a selected OPS, to have a positive (sourcing current), negative (sinking current), or off (no current) polarity in any of the k channels.

Moreover, it is seen that each of the n electrode contacts can operate in a bipolar mode or multipolar mode, e.g., where two or more electrode contacts are grouped to source/sink current at the same time. Alternatively, each of the n electrode contacts can operate in a monopolar mode where, e.g., the electrode contacts associated with a channel are configured as cathodes (negative), and the case electrode, on the IPG case, is configured as an anode (positive). The mode of the electrode contacts that is to be used, e.g., bipolar, multipolar or monopolar, may also be defined by a specific parameter included within the current OPS.

Further, the amplitude of the current pulse being sourced or sunk from a given electrode contact may be programmed to one of several discrete levels. These discrete levels may be similarly defined by a specific parameter, or a specific group of parameters, included within the current OPS. In one embodiment, the currents can be individually set from ±0 to ±12.7 mA, in steps of 0.1 mA. In another embodiment, at least one channel of electrodes is capable of an output of at least ±20 mA (distributed among the electrodes included in the channel group). The current output capacity of individual electrodes are limited when operating with more than one other electrode of the same polarity in a given channel in order to assure that the maximum current values are maintained. Additionally, in order to prevent unpleasant sensations due to sudden changes in current amplitude, amplitude changes are preferably gradually changed, e.g., in a ramping fashion, at a specified "ramp rate", between the value range between the settings. The ramp rate may also be defined by a specific parameter included within the current OPS. Such ramping feature may also be used when initially powering on the IPG, thereby preventing full magnitude stimulus pulses from being delivered to the patient during a ramping-up time period. The ramp rate may be different, as defined by the current OPS, depending upon the channel and programmed amplitude, between about 1 and 10 seconds.

Also, the pulse width of the current pulses is adjustable in convenient increments. As with the other operational parameters associated with the IPG, the pulse width may be defined by a specific parameter included within the current OPS. The pulse width range is preferably at least 0 to 1 ms in increments of 10 $\mu$s. Generally, it is preferred that the pulse width be equal for all electrodes in the same channel.

Similarly, the pulse rate is adjustable within acceptable limits. The pulse rate may likewise be defined by an appropriate parameter included within the current OPS. The pulse rate preferably spans at least two ranges: (1) a normal rate; and (2) a high rate. The normal rate range covers 0–150 pps per channel in approximately 1 pps increments. The high rate range covers 100–500 pps in increments of approximately 10 pps, and generally need only be available on one or two channels. When used, the high rate range limits operation of the additional channels at the normal rates when stimulation and/or power conflicts are determined to be present.

Because the IPG 100, or the IPG 100', is typically only capable of delivering current pulses up to ±20 mA in amplitude at any instant in time, the SCS system also regulates the channel rates to prevent overlap (i.e., to prevent two or more pulses from different channels from occurring at the same time). Such channel rate regulation is transparent to the patient.

The stimulation pulses generated by the IPG 100 or the IPG 100' should also be charged balanced. This means that the amount of positive charge associated with a given stimulus pulse should be offset with an equal and opposite negative charge. Charge balance may be achieved through a coupling capacitor, which provides a passive capacitor discharge that achieves the desired charge balanced condition. Such passive capacitor discharge is evident in the waveforms depicted in FIG. 3 as the slowly decaying waveform following the short trailing edge of each pulse. Alternatively, active biphasic or multiphasic pulses with positive and negative phases that are balanced may be used to achieve the needed charge balanced condition.

In some embodiments of the invention, a real-time clock is also incorporated within the timing circuits of the IPG 100 or the IPG 100'. Such real-time clock advantageously allows a run schedule to be included within the current OPS. That is, the patient can schedule auto-run times for IPG operation at certain times of the day. When an auto-run time begins, all channels are enabled and provide a previously-programmed pattern of stimulus currents, i.e., current pulses having a programmed width, rate, and amplitude are generated and delivered through each channel. The auto-run time continues for a set time period, e.g., several hours, or for only a few minutes. Advantageously, the auto-run time is defined by the current OPS. Thus, when a new OPS is selected to replace an existing OPS, the new OPS controls operation of the IPG thereafter, including any auto-run time that may be defined in the new OPS.

A feature that may be included within the IPG 100 or IPG 100' is the ability to measure electrode impedance, and to transfer the impedance thus measured back to a remote programmer, or other processor, through the forward/back telemetry circuits 172. Also, the microcontroller 160, in combination with the other logic circuits, may also be programmed to use the electrode impedance measurements to adjust compliance voltages and to thereby better maintain low battery consumption. In one embodiment of the IPG 100 or IPG 100', electrode impedance is measured for each electrode contact by sourcing or sinking a 4 mA current pulse from the electrode contact to the case electrode, measuring the voltage at the electrode contact, and computing the resulting impedance. (Impedance is equal to voltage/current.) For a spinal cord implantation, the electrode impedance will typically range between about 400 ohms and 600 ohms, as measured between a selected electrode contact to the indifferent case electrode.

Advantageously, by using current sources of the type disclosed in the referenced patent application, or similar current sources, the IPG 100 or 100' is able to individually control the n electrode contacts associated with the n electrode nodes E1, E2, E3, . . . En. Controlling the current sources and switching matrix 188 (for the IPG 100 shown in FIG. 4), or controlling the current source DACs 191 and 193 (for the IPG 100' shown in FIG. 5), using the microcontroller 160, as defined by individual operational parameters included within the current OPS, in combination with the control logic 166 and timer logic 168, thereby allows each electrode contact to be paired or grouped with other electrode contacts, including the monopolar case electrode, in order to control the polarity, amplitude, rate, pulse width and channel through which the current stimulus pulses are provided.

As shown in FIG. 4 and/or FIG. 5, much of circuitry included within the IPG 100 or 100' may be realized on a single application specific integrated circuit (ASIC) 190. This allows the overall size of the IPG to be quite small, and readily housed within a suitable hermetically-sealed case. The IPG 100 or 100' includes n feedthroughs to allow electrical contact to be individually made from inside of the hermetically-sealed case with the n electrodes that form part of the lead system outside of the case. The IPG case is preferably made from titanium and is shaped in a rounded case. A exemplary rounded IPG case has a maximum circular diameter of about 50 mm, and preferably only about 45 mm (or equivalent area). Thus, the implant case has smooth curved transitions that minimize or eliminate edges or sharp corners. The maximum thickness of the case is about 10 mm, and is preferably only about 8 mm.

It is thus seen that the implant portion 10 of the SCS system (see FIG. 1) includes an implantable pulse generator (IPG) 100 as described in FIG. 4, or an IPG 100' as described in FIG. 5. Such IPG further includes stimulating electronics (comprising programmable current sources and associated control logic), a power source, and a telemetry system. Advantageously, the power source may be recharged over and over again, as needed, and may thus provide a long life, as well as a high current output capacity.

A feature of the SCS system is its ability to map current fields through selective control of the current sources which are attached to each electrode node. Independent current mapping is achieved by directing a desired current to each electrode node through the use of a microcontroller 160, one or more ASIC's, a multiplicity of positive and negative current DACs, timers and control registers, and a state machine architecture. The ASIC has a standard bus interface to the microcontroller allowing simple, direct and efficient access to all of its control and stimulation parameter registers. Each current DAC is capable of driving a 1 Kohm load with constant current biphasic pulses up to 12.7 mA with 7 bit resolution, 1 bit accuracy, at phase durations up to 1000 $\mu$s with 1 $\mu$s resolution. Each current DAC is independent of the other current DACs, but any of the DACs may be linked in the triggering (control) circuitry and/or their outputs may be linked. Triggering and timing control circuitry allow the simultaneous activation of any of the channels. One or more current DACs may be attached to any one or more electrode nodes (leadwires) and thus electrodes, and conversely, any electrode node (leadwire) may be attached to a positive or negative current DAC, grounded, or left open. The significance of the biphasic, or (in some instances) multiphasic, nature of the stimulation pulses is that currents may be actively driven in either the anodic or cathodic direction to the output electrode nodes of the current DACs. This feature along with independent enabling of the output current DACs allows the creation of "virtual" electrodes and stimulation current field control, not possible with other known designs. This feature thus provides an important advance in the ability to direct the stimulation pulses to pools of target neurons in the spinal cord or other target tissue.

In use, the IPG 100 or IPG 100' is placed in a surgically-made pocket either in the abdomen, or just at the top of the buttocks, and detachably connected to the lead system (comprising lead extension 120 and electrode array 110). While the lead system is intended to be permanent, the IPG may be replaced should its power source fail, or for other reasons. Thus, a suitable connector, e.g., the snap-on tool-less connector disclosed in U.S. patent application Ser. No. 09/239,926, filed Jan. 28, 1999, or other suitable connectors, may advantageously be used to make the connection between the lead system and the IPG 100 or 100'. The '926 patent application is incorporated herein by reference.

Once the IPG 100 or 100' has been implanted, and the implant system 10 is in place, the system may be programmed to provide a desired stimulation pattern at desired times of the day. The stimulation parameters are defined in an operational parameter set (OPS), which may also be referred to as an "operational parameter data set", or "controlling data." The parameters defined by and included within the operational parameter data set may include, e.g., the number of channels (defined by the selection of electrodes with synchronized stimulation), the stimulation rate and the stimulation pulse width. Also, the operational parameter data set defines the current output from each electrode by polarity and amplitude. Additionally, as indicated above, a run schedule may be defined in the operational parameter data set, which when used enables the IPG only at programmed times of the day.

The back telemetry features of the IPG 100 or IPG 100' allow the status of the IPG to be checked. For example, when the external hand-held programmer 202 (and/or the clinician programmer 204) initiates a programming session with the implant system 10 (FIG. 1), the capacity of the battery is telemetered so that the external programmer can calculate the estimated time to recharge. Additionally, the electrode impedance measurements are telemetered at the beginning of each programming session, or as requested. Any changes made to the current stimulus parameters are confirmed through back telemetry, thereby assuring that such changes have been correctly received and implemented within the implant system. Moreover, upon interrogation by the external programmer, all programmable settings stored within the implant system 10 may be uploaded to one or more external programmers.

A clinician programming system, as seen in FIG. 1, is preferably used with the IPG 100 or 100'. Such clinician programming system includes a clinician programmer 204 coupled to a directional device 206. The clinician programmer 204 typically interfaces with a patient hand-held programmer (HHP) 202 in communicating with the IPG 100 or 100'. It should be noted that the clinician's programming system represents one way in which the IPG 100 or 100' may be programmed, but not the only way. Those of skill in the art should be able to fashion various ways in which the IPG 100 or 100' could be programmed.

The clinician's programming system optimizes the programming of the IPG for the patient. The programming system maintains a patient data base, and is able to program all features of the implant device in a simple and intuitive manner. Additionally, the system allows threshold measurements to be made, operational electrodes to be identified, and is able to interface directly with the patient.

One feature of the SCS programming system is the use of a joystick accessory, or equivalent directional device 206 (FIG. 1), which allows the clinician to interface with a laptop computer (e.g., programmed to function as the clinician programmer 204), or other processor (e.g., a hand-held computer, such as a PalmPilot® computer, or equivalent) so as to allow the clinician, or other medical personnel assisting the clinician, to configure electrodes and adjust various stimulation parameters. A suitable directional programming device is described in more detail in U.S. Pat. No. 6,052,624, "Directional Programming for Implantable Electrode Arrays", which patent is incorporated herein by reference. As described in the '624 patent, such directional programming may advantageously be performed either in the operating room (OR) environment and in the doctor's office. The clinician or nurse simply operates the joystick feature, or equivalent directional programming feature, during surgery in conjunction with the trial stimulator 140 so as to configure and select the electrodes that provide desired stimulation. The clinician then uses the joystick feature to finalize the device programming during a post implant adjustment session. Thus, whether communicating with the trial stimulator 140 or with the IPG 100, the directional programming device 206 is able to be effectively used to configure which electrodes provide stimuli to the patient.

In operation, as seen in FIG. 1, the clinician programming system communicates to the patient HHP 202 over a telecommunicative or other communication link 203, which then telemeters the data to the IPG 100 or 100'. Likewise, the clinician's programmer is able to communicate to the trial stimulator 140 over the telecommunicative link 205. The communication links 203 and 205 are reliable links capable of operating in the busy OR environment. Data speeds to and from the IPG, through the patient programmer 202 intermediary link, are fast enough to not noticeably delay programming. A communication link status between devices is always depicted on a screen, or other display device, associated with the programmer 204.

As soon as the clinician programmer is initially connected to the implant system, hardware recognition occurs. That is, the system identifies the stimulator, the patient programmer, and electrode availability (through electrode impedance measurements).

For safety, the HHP 202 is coded to work only with a specific implant system. Should the patient lose his or her programmer 202, then the physician, using the clinician programmer, is able to code a new programmer for use with the patient's implant system. The clinician's programmer, in contrast, is able to communicate to any implant through any HHP 202 by using an overriding universal code. This allows the patient code to be extracted from the IPG 100 and used to re-code a new HHP 202.

When an IPG 100 or 100' is in contact with a clinician programmer 204, the device settings and hardware information (model, serial number, number of electrode by impedance, and the like) are first uploaded to the clinician programmer 204. All devices in the link with the IPG, e.g., the HHP 202, and/or the trial stimulator 140, and clinician programmer 204, are synchronized so that each device receives accurate and current data. Programming changes made to the stimulator(s) are confirmed through back telemetry or other means before the SCS system software reflects the change. Advantageously, the physician is able to program the stimulator through either the patient HHP 202 or the clinician programmer 204 while linked together through the link 203, with all programming changes being mirrored in both devices.

Additional details associated with the Clinician's programming system, including the hand-held programmer (HHP) 202 used therewith, are more fully described in the previously referenced U.S. patent application Ser. No. 09/626,010. The details associated with the use and operation of the clinician programming system and HHP 202 are not relevant to the present invention, and thus are not described herein in any great detail.

By way of overview, it is noted that the HHP 202 is small enough to be held comfortably in one hand. It has a flat panel display that shows programmable values as they are selected and/or modified. As desired, it may be inserted into a cover-case which protects the buttons from being inadvertently pressed. It further includes an accessible battery compartment which allows its batteries to be replaced, as needed. The buttons or other controls used on the handheld programmer are easy to manipulate, and provide immediate access (without scrolling and selecting) to ON/OFF, amplitude, pulse width and rate settings. A visual display provided as an integral part of the handheld programmer clearly labels each parameter with the associated control button, and displays large characters for easy viewing. The handheld programmer reliably programs the IPG from a specified distance, e.g., 12–24 inches, and actively displays the status of the communication link with the IPG. Further, when used as a relay device between the clinician's programmer 204 and the IPG 100, the handheld programmer 202 provides a data rate and loop speed that is sufficiently fast so that the patient can make programming selecting changes and quickly feel the result. As a safety feature, any given handheld programmer 202 is able to communicate only with one IPG when operated by the patient, whereas a physician (when a hidden physician screen is activated) may use the handheld programmer 202 to communicate universally with any IPG.

Figure 6:
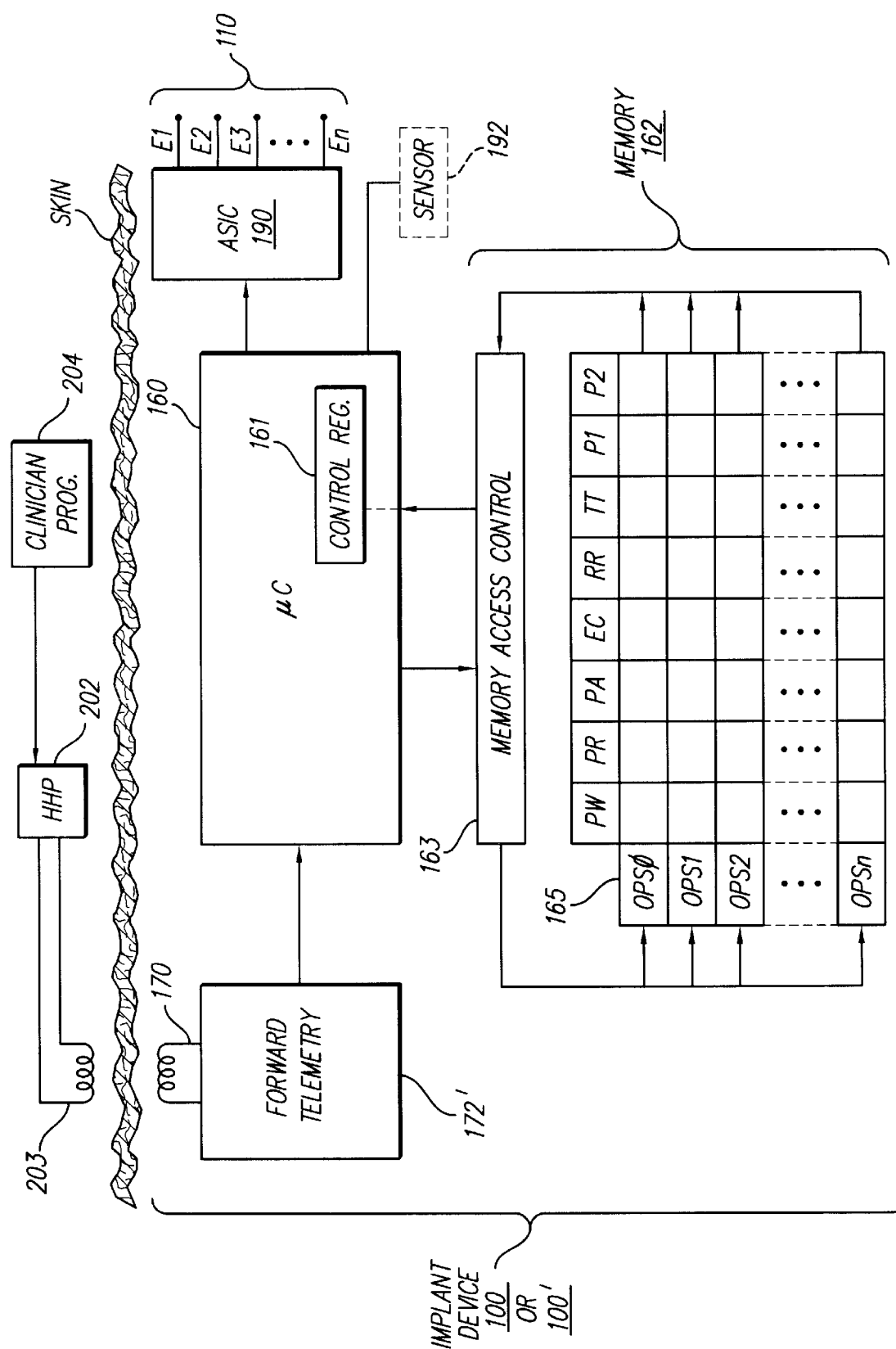
FIG. 6 depicts a functional block diagram of a portion of an implant device, e.g., the IPG of FIG. 4 or FIG. 5, and functionally illustrates one manner in which different operational parameter sets may be selected for use by the implant device.

Next, with reference to FIG. 6, there is shown a block diagram of a portion of the implant device, or IPG 100 or 100', that functionally illustrates one manner that may be used in accordance with the present invention to allow the patient user to select one of a plurality of operational parameter sets (OPS's), for use by the implant device. As seen in FIG. 6, and as explained previously in connection with FIG. 4 or FIG. 5, the implant device 100 or 100' includes a coil 170 that receives modulated RF signals from an external hand-held programmer (HHP) 202. The data that modulates the RF signal transmitted by the HHP 202 may originate from within the HHP 202, or may originate from a clinician programmer 204, or an equivalent source.

The modulated RF signal is received through receiving coil 170 and processed by the forward/back telemetry circuit 172'. Informational data contained within the modulation of the RF signal is demodulated and forwarded to the microcontroller ($\mu C$) 160. The $\mu C$ 160, in turn, acts on the data in an appropriate manner. Some data, for example, is data that defines operational parameters that are used within the implant device 100 or 100' to control its operation in accordance with an operating program stored in its memory 162. Such data is forwarded to appropriate locations within a memory 162, which specified locations may be considered as a memory table 165, through a memory access control circuit 163. The memory table 165 includes individual addressable locations wherein various operational parameters may be stored. A first operational parameter, for example, may comprise data that defines the pulse width (PW) of a stimulation pulse. Yet other operational parameter data may define the pulse rate (PR), pulse amplitude (PA), electrode configuration (EC), ramp rate (RR), treatment times (TT), a first other parameter (P1), and a second other parameter (P2), and the like, associated with a stimulation pulse sequence. All such data, when combined, thus define an operational parameter set (OPS) that may be used by the implant device 100 or 100' as it provides stimulation pulses through selected electrodes E1, E2, . . . En of the electrode array 110. The particular OPS used to control the operation of the implant device 100 or 100' is retrieved from memory 162 through memory access control 163 and held in a control register 161, or equivalent holding location. If is from the control register 161 that the individual operational parameters contained within the selected OPS interact with the application specific integrated circuit(s) (ASIC) 190, including the control logic 166 and timer logic 168 included within the ASIC 190 (see FIG. 4 or FIG. 5), to generate stimulation pulses defined by the OPS held in the control register 161.

As seen in FIG. 6, in accordance with the embodiment of the invention shown in FIG. 6, a plurality of different operational parameter sets, e.g., OPS0, OPS1, OPS2, . . . OPSn, where n is an integer, typically equal to at least four, are stored within the memory 162 of the implant device 100 or 100' (or within the memory of the HHP 202, as described below). When the patient user wants to select a different OPS for controlling the implant device, he or she, using manual selection controls on the HHP 202 selects one of the plurality of OPS's, e.g., OPS3, that is stored within the implant device. An appropriate selection signal is then sent to the $\mu C$ 160 within the implant device 100 via the coils 203 and 170 and forward telemetry circuitry 172'. Such selection signal steers the memory access control circuit 163, causing it to retrieve the selected operational parameter set, e.g., OPS3, from the memory table 165 and to load it into the control register 161, from which location it thereafter controls the operation of the implant device 100. In this manner, the patient user is able to easily select a desired operational parameter set for use by the implant device.

Advantageously, all of the individual parameters included within each OPS stored within the memory 162 are pre-screened, prior to allowing such to be stored in the memory table 165, to be within acceptable, safe limits. In practice, most of these operational parameters, if not all, are initially defined by the clinician using the clinician programmer 204 that is coupled to the implant device 100 or 100' through the HHP 202. As part of the initial selection process, the clinician programmer 204 maintains the parameters within set limits, or the physician (the one using the clinician programmer), attaches appropriate limits to each parameter.

As further seen in FIG. 6, the implant device 100 or 100' may also have a sensor 192 coupled to the $\mu C$ 160. Such sensor 192 may actually be housed within the same housing as the implant device, or it may be housed within a separate housing that is coupled with the implant device. The sensor 192 is configured to sense an appropriate event, such as: a certain body temperature; a certain glucose level in the body tissue or blood; a certain pH level of the body tissue or blood; a certain pulse rate or respiration rate; a certain body position, e.g., horizontal; a certain mechanical thumping (as when the patient taps a finger on the skin above where the implant device is implanted); a certain audible tone, a certain elapsed time or attainment of a certain time of day, and similar events. Some embodiments may include multiple sensors, in which case the occurrence of the "event" may actually be the occurrence of a prescribed combination of several events. The sensing of the prescribed "event" by the sensor 192, in turn, automatically triggers the use of a prescribed OPS. That is, as soon as the "event" is detected by the sensor 192, the $\mu C$ 160 responds by directing the memory access control circuit 163 to retrieve the appropriate OPS from the memory table 165 and load it into the control register 161.

Figure 7:
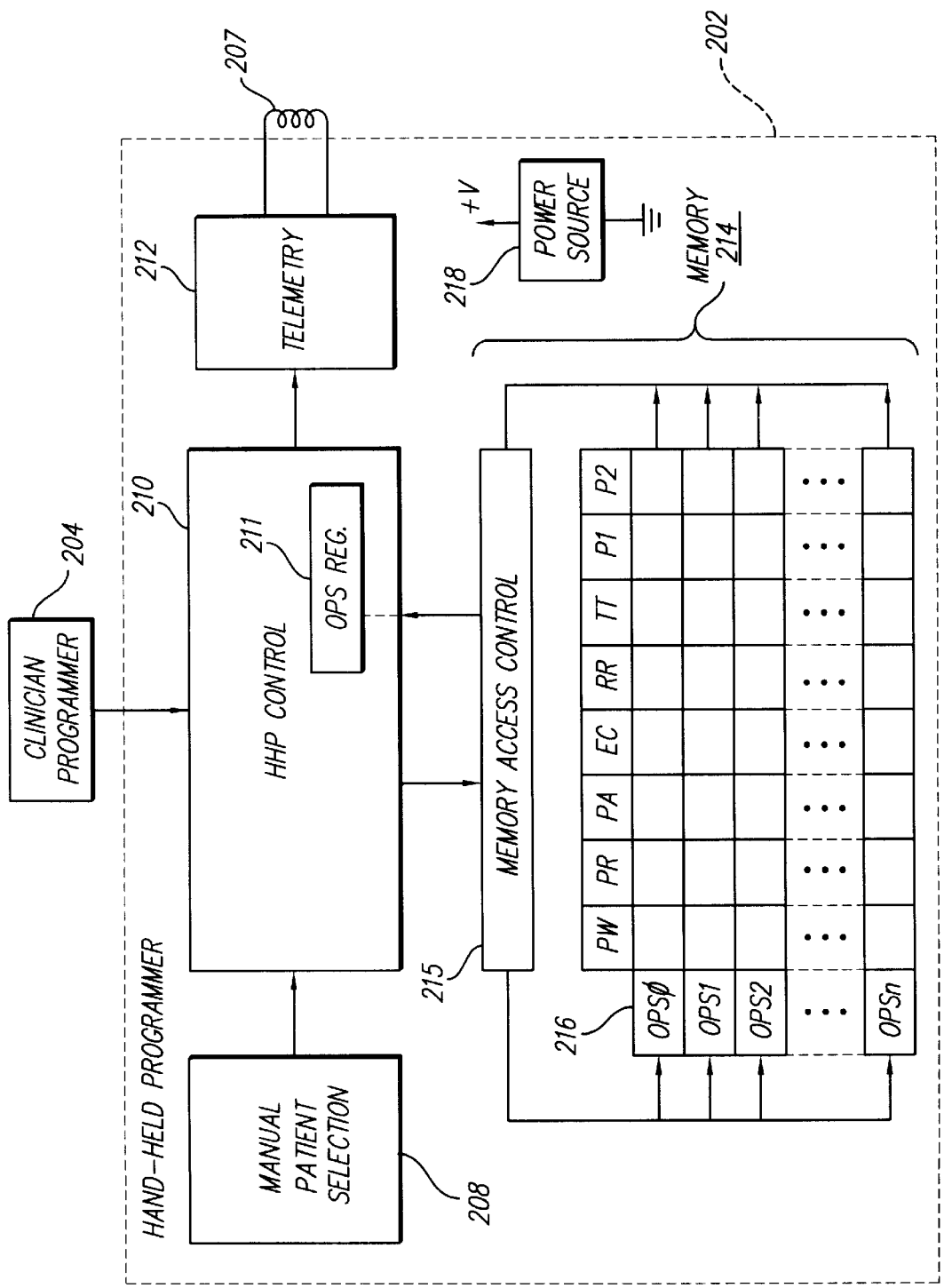
FIG. 7 shows a functional block diagram of a portion of an external programming device, e.g., a hand-held programmer, and functionally illustrates another manner in which different operational parameter sets may be selected for use by the implant device.

Next, with reference to FIG. 7, an alternative embodiment of the invention is shown. In the embodiment shown in FIG. 7, a plurality of OPS's are stored within a section or area (e.g., a table) 216 of a memory 214 of the hand-held programmer (HHP) 202. The patient user selects one of the plurality of OPS's as the desired OPS through appropriate manual patient selection means 208 included as part of the HHP 202. Such means typically comprise pressing appropriate keys or buttons on a keypad, or display screen, but any suitable input means may be used. Once the desired OPS has been selected, an HHP control circuit 210 directs a memory access control circuit 215 to retrieve the selected OPS from the memory table 216 and store it in an OPS register 211 that forms part of the HHP 210. The OPS held in the OPS register 211 is then downloaded, through the telemetry circuit 212 and coil 207, to the implant device 100 or 100'. When received within the implant device 100 or 100', it is loaded into a control register within the microcontroller 160 of the implant device, from which location it controls the operation of the implant device, as described previously.

All of the individual parameters included within each OPS stored within the memory 214 are pre-screened, prior to allowing such to be stored in the memory table 216, so as to assure that they are within acceptable, safe limits.

The HHP 202 shown in FIG. 7 further includes a suitable power source 218, e.g., a replaceable or rechargeable battery, that is used to provide the operating power for the HHP, including the transmission of modulated RF signals to the implant device.

For the embodiment shown in FIG. 7, a sensor 192 (see FIG. 6) may still be employed within the implant device 100 or 100' to detect the occurrence of a prescribed "event". In such instance, the back telemetry features of the implant device 100 (see FIG. 4), or the implant device 100' (see FIG. 5, may be used to signal the HHP 202 of the occurrence of the event. The occurrence of the event, in turn, could trigger the HHP controller 210 to retrieve the appropriate OPS from memory, and download it through the telemetry circuits 212 and 172 (FIG. 4) to the implant device, from which location it controls the operation of the implant device, as described above.

Figure 8:
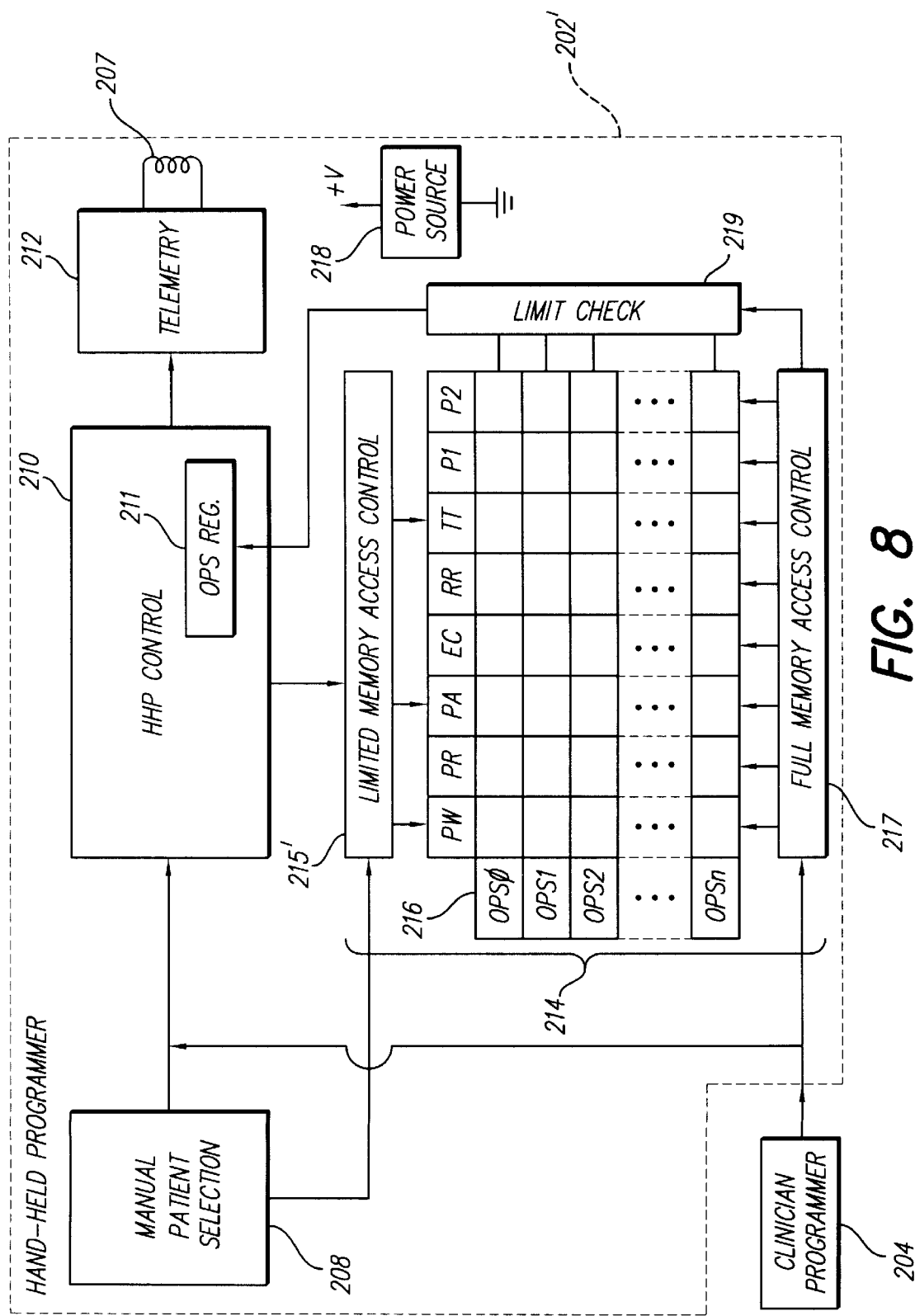
FIG. 8 illustrates a functional block diagram of a portion of an external programming device, e.g., a hand-held programmer, and functionally illustrates how the invention allows the patient to define a new operational parameter set, yet restricts individual parameter values within the newly defined operational parameter set to be within prescribed limits.

Turning next to FIG. 8, a further feature of the invention is functionally depicted to illustrate one manner in which the patient user may define new programs, e.g., new OPS's, for use by the implant device 100 or 100'. FIG. 8 shows a functional diagram of another embodiment of a hand-held programmer (HHP) 202'. The HHP 202' shown in FIG. 8 may in practice be the same HHP 202 shown in FIG. 7, with additional functions provided or activated. The additional functions added or activated in FIG. 8 include the use of a limited memory access control circuit 215', a full memory access control circuit 217, and a limit check circuit 219, all of which are used as part of, or in conjunction with, the memory 214.

With reference to FIG. 8, the configuration shown therein allows the HHP user to selectively set the values of certain ones of the operational parameters that are included within any of the stored OPS's. This is done through activation of the limited memory access control circuit 215', which enables the user to access only certain ones of the operational parameters stored in the memory table 216. By way of illustration, as shown in FIG. 8, the HHP user is only able to access the parameters PW, PA and TT. The other parameters included within a given OPS can only be programmed or altered through the clinician programmer 204 and the full memory access control circuit 217. Thus, in this way, a physician, using the clinician programmer 204, is able to initially define the operational parameter sets, OPS0, OPS1, OPS2, . . . OPSn, that are stored within the memory table 216. The user patient is thereafter able to selectively change certain ones of the parameters within each OPS, e.g., PW, PA and TT, through use of the manual patient selection means 208 and limited memory access control circuit 215'.

As selected OPS's are retrieved from the memory table 216, they pass through the limit check circuit 219. The limit check circuit 219 compares the value of each parameter included within the selected OPS to make sure that it is kept within prescribed limits. If it is not within limits, then the parameter is clipped, i.e., it is set to the limit value closest to the parameter value that exceeds the limit. The OPS, with all parameter values thus checked and clipped, as required, so as to be within prescribed limits, is then passed to the OPS register 211, or equivalent holding area within the HHP controller 210, from which location it is downloaded to the implant device and used therein to control the operation of the implant device.

Those of skill in the art will readily recognize that the descriptions presented herein, particularly relative to FIGS. 6, 7 and 8, are functional in nature. The actual hardware, firmware, and/or software devices, circuits, and/or processors used to implement the functions shown in these functional figures may take numerous forms and types. The present invention is intended to cover all such implementations, regardless of form.

Thus, while the invention herein disclosed has been described by means of specific embodiments and applications thereof, numerous modifications and variations may be made thereto by those skilled in the art without departing from the scope of the invention set forth in the claims.

What is claimed is:

1. An implant device comprising:
    an implantable case;
    electronic circuitry housed within said implantable case for performing a prescribed function, the electronic circuitry including
        a control register wherein a control set of operational parameters is stored,
        a controller that controls the operation of the implant device as a function of the control set of operational parameters stored in the control register, and
        a plurality of sets of operational parameters; and
    selection means for selecting one of the plurality of sets of operational parameters as the control set of operational parameters that is stored in the control register;
    whereby the operation of the implant device may be changed through selection of a different set of operational parameters.

2. The implant device of claim 1 wherein the electronic circuitry further includes memory circuitry wherein the plurality of sets of operational parameters are stored, and wherein the selection means comprises memory access control means for retrieving a selected set of operational parameters from the memory circuitry and loading it into the control register.

3. The implant device of claim 1 wherein the selection means comprises:
    memory means external to the implant device wherein the plurality of sets of operational parameters are stored; and
    telemetry means for transmitting a selected one of the plurality of sets of operational parameters to the electronic circuitry for loading into the control register.

4. The implant device of claim 1 further including change means for allowing a user of the implant device to change individual parameters included within a selected one of the plurality of operational parameters.

5. The implant device of claim 4 wherein the change means allows the user of the implant device to change only certain ones of the individual parameters included within the selected one of the plurality of operational parameters.

6. The implant device of claim 1 wherein the prescribed function performed by the electronic circuitry comprises a stimulation pulse generator, and wherein the operational parameters included within the control set of operational parameters include pulse width, pulse amplitude and pulse rate.

7. The implant device of claim 6 wherein the operational parameters included within the control set of operational parameters further include electrode configuration, ramp rate, and treatment time.

8. A method of changing the operational parameters used to control an implant device, comprising:
    defining a plurality of sets of operational parameters, each set including individual parameters that define respective characteristics associated with the operation of the implant device;
    storing the plurality of sets of operational parameters;
    selecting one of the stored sets of operational parameters as a control set of operational parameters; and
    providing the control set of operational parameters to the implant device, and using the provided control set of operational parameters to control the operation of the implant device.

9. The method of claim 8 wherein the defining step comprises defining each set of the plurality of sets of operational parameters so that each of the individual parameters within each set are within prescribed safe operating limits.

10. The method of claim 9 wherein the storing step comprises storing each of the sets of operational parameters within memory circuitry included within the implant device.

11. The method of claim 9 wherein the storing step comprises storing each of the sets of operational parameters within memory circuitry that is external to the implant device.

12. The method of claim 9 further including allowing a user of the implant device to define a new set of operational parameters that replaces an existing set of operational parameters.

13. The method of claim 9 further including the step of limiting changes made to a set of operational parameters to changes in just prescribed ones of the individual parameters included within the set of operational parameters.

14. An implant system that permits parameter context switching comprising:
    an implant device comprising:

electronic circuitry that performs a prescribed function as controlled by a set of operational parameters, a first memory element wherein the set of operational parameters is stored, a replenishable power source that provides operating power for the implant device, a first telemetry circuit that receives control data from an external source, and a second telemetry circuit that receives power to replenish the replenishable power source;

an external control device comprising a first transmission circuit that transfers control data through the first telemetry circuit of the implant device that defines the set of operational parameters stored in the first memory element of the implant device; and an external charging device comprising:
a power source, and
a second transmission circuit that transfers power from the power source through the second telemetry circuit to the replenishable power source of the implant device.

15. The implant system of claim 14 wherein the first memory element within the implant device has a plurality of sets of operational parameters stored therein, and wherein the external control device transfers control data to the implant device that selects one of the plurality of sets of operational parameters as a control set of operational parameters to be used to control the electronic circuitry.

16. The implant system of claim 14 wherein the external control device includes a second memory element wherein a plurality of sets of operational parameters are stored, and further wherein the external control device includes means for selecting one of the plurality of sets of operational parameters and sending the selected set of operational parameters to the implant device for storage in the first memory means, from which location the selected set of operational parameters controls the operation of the electronic circuitry within the implant device.

17. The implant system of claim 16 further including:

limited memory access control circuitry within the external control device that allows access to a selected plurality of individual operating parameters within each of the sets of operational parameters included within the plurality of sets of operational parameters stored within the second memory element;

full memory access control circuitry within the external control device that allows access to all of the individual operating parameters of each of the sets of operational parameters included within the plurality of sets of operational parameters stored within the second memory element;

a manual patient selection circuit that allows a patient user of the external control device to selectively alter the selected plurality of individual operating parameters accessible through the limited memory access control circuitry; and a clinician programmer selectively coupled to the full memory access control circuitry that allows a clinician user of the clinician programmer to selectively alter all of the individual operating parameters of each of the sets of operational parameters included within the plurality of sets of operational parameters stored within the second memory element.

18. The implant system of claim 17 wherein the external control device further includes limit checking circuitry that prevents an alteration of individual operating parameters contained within the plurality of sets of operational parameters that exceeds a respective predefined limit.

* * * * *

(12) INTER PARTES REVIEW CERTIFICATE (2846th)
United States Patent (10) Number: US 6,381,496 K1
Meadows et al. (45) Certificate Issued: Sep. 28, 2022

(54) PARAMETER CONTEXT SWITCHING FOR AN IMPLANTED DEVICE

(75) Inventors: Paul A. Meadows; Carla M. Mann

(73) Assignee: BOSTON SCIENTIFIC NEUROMODULATION CORPORATION

Trial Number:

IPR2019-01340 filed Jul. 18, 2019

Inter Partes Review Certificate for:

Patent No.: 6,381,496
Issued: Apr. 30, 2002
Appl. No.: 09/668,925
Filed: Sep. 25, 2000

The results of IPR2019-01340 are reflected in this inter partes review certificate under 35 U.S.C. 318(b).

INTER PARTES REVIEW CERTIFICATE
U.S. Patent 6,381,496 K1
Trial No. IPR2019-01340
Certificate Issued Sep. 28, 2022

AS A RESULT OF THE INTER PARTES REVIEW PROCEEDING, IT HAS BEEN DETERMINED THAT:

Claims 1-18 are cancelled.

\* \* \* \* \*